(12) United States Patent
Berg et al.

(10) Patent No.: US 9,764,251 B2
(45) Date of Patent: Sep. 19, 2017

(54) INTRODUCING SAMPLES INTO SUPERCRITICAL FLUID CHROMATOGRAPHY SYSTEMS

(71) Applicant: Waters Technologies Corporation, Milford, MA (US)

(72) Inventors: Emily J. Berg, Milford, MA (US); Joshua A. Shreve, Franklin, MA (US); James E. Usowicz, Webster, MA (US); Douglas P. Wittmer, Shrewsbury, MA (US); Aaron Lebeau, Taunton, MA (US)

(73) Assignee: Waters Technologies Corporation, Milford, MA (US)

( * ) Notice: Subject to any disclaimer, the term of this patent is extended or adjusted under 35 U.S.C. 154(b) by 328 days.

(21) Appl. No.: 14/383,239

(22) PCT Filed: Mar. 5, 2013

(86) PCT No.: PCT/US2013/029048
§ 371 (c)(1),
(2) Date: Sep. 5, 2014

(87) PCT Pub. No.: WO2013/134222
PCT Pub. Date: Sep. 12, 2013

(65) Prior Publication Data
US 2015/0047422 A1 Feb. 19, 2015

Related U.S. Application Data

(60) Provisional application No. 61/608,135, filed on Mar. 8, 2012.

(51) Int. Cl.
*G01N 1/00* (2006.01)
*B01D 15/14* (2006.01)
(Continued)

(52) U.S. Cl.
CPC ............ *B01D 15/14* (2013.01); *B01D 15/40* (2013.01); *G01N 30/16* (2013.01); *G01N 30/20* (2013.01);
(Continued)

(58) Field of Classification Search
CPC ...... G01N 30/02; G01N 30/32; G01N 30/461; G01N 30/24; G01N 30/34; G01N 30/36;
(Continued)

(56) References Cited

U.S. PATENT DOCUMENTS

| 4,984,602 A | 1/1991 | Saito et al. |
|---|---|---|
| 5,234,599 A | 8/1993 | Cortes et al. |

(Continued)

FOREIGN PATENT DOCUMENTS

| FR | 2 960 643 A1 | 12/2011 |
|---|---|---|
| JP | 62-027660 A | 2/1987 |

(Continued)

OTHER PUBLICATIONS

International Search Report for Application No. PCT/US2013/29048, mailing date of May 20, 2013, 4 pages.
(Continued)

*Primary Examiner* — John Fitzgerald
*Assistant Examiner* — Truong Phan
(74) *Attorney, Agent, or Firm* — Waters Technologies Corporation

(57) ABSTRACT

A supercritical fluid chromatography system is provided with an injection valve subsystem for introducing a sample into a flow of mobile phase fluid. The injection valve subsystem includes an auxiliary valve and an inject valve. The operations of the auxiliary and inject valves are coordinated in such a manner as to reduce sample carry-over and system pressure perturbations occurring during sample injection.

20 Claims, 14 Drawing Sheets

(51) Int. Cl.
  *B01D 15/40* (2006.01)
  *G01N 30/20* (2006.01)
  *G01N 30/16* (2006.01)
  *G01N 30/28* (2006.01)

(52) U.S. Cl.
  CPC ....... *G01N 30/28* (2013.01); *G01N 2030/201* (2013.01); *G01N 2030/202* (2013.01); *G01N 2030/207* (2013.01)

(58) Field of Classification Search
  CPC ..... G01N 30/56; B01D 15/08; B01J 2220/54; B01J 20/32
  USPC ........ 73/61.52, 61.55, 61.56; 210/656, 198.2
  See application file for complete search history.

(56) References Cited

U.S. PATENT DOCUMENTS

| | | | |
|---|---|---|---|
| 6,428,702 | B1 | 8/2002 | Berger et al. |
| 2003/0034307 | A1 | 2/2003 | Berger et al. |
| 2006/0249459 | A1* | 11/2006 | Matabe .................. G01N 30/22 210/656 |
| 2009/0050212 | A1 | 2/2009 | Dourdeville |
| 2011/0247403 | A1 | 10/2011 | Liu |
| 2011/0315633 | A1 | 12/2011 | Cormier |
| 2012/0006750 | A1* | 1/2012 | Miyazawa ............. B01D 15/40 210/656 |

FOREIGN PATENT DOCUMENTS

| | | |
|---|---|---|
| JP | 06-502495 A | 3/1994 |
| JP | 2008-529010 A | 7/2008 |
| WO | 92/05852 A1 | 4/1992 |
| WO | 2006/083776 A2 | 8/2006 |
| WO | 2010/051005 A2 | 5/2010 |
| WO | 2010/118414 A1 | 10/2010 |
| WO | 2012027632 | 3/2012 |

OTHER PUBLICATIONS

International Written Opinion Report for Application No. PCT/US2013/29048, mailing date of May 20, 2013, 9 pages.

Extended European Search Report for Application No. 13757550.2, issued Nov. 26, 2015 (10 pages).

Japanese Office Action for Application No. 2014-561021, issued Jan. 10, 2017 (19 pages).

* cited by examiner

INTRODUCING SAMPLES INTO SUPERCRITICAL FLUID CHROMATOGRAPHY SYSTEMS

RELATED APPLICATIONS

This application is the National Stage of International Application No. PCT/US2013/029048, filed on Mar. 5, 2013, which claims priority to and benefit of U.S. Provisional Patent Application No. 61/608,135 entitled "Introducing Samples into Supercritical Fluid Chromatography Systems," filed Mar. 8, 2012. The contents and teachings of each of these applications are hereby expressly incorporated herein by reference in their entirety.

TECHNICAL FIELD

This disclosure relates to introducing samples into supercritical fluid chromatography systems.

BACKGROUND

Supercritical fluid chromatography (SFC) is a chromatographic separation technique that typically utilizes liquefied carbon dioxide ($CO_2$) as a mobile phase solvent. In order to keep the mobile phase in liquid (or liquid-like density) form, the chromatographic flow path is pressurized; typically to a pressure of at least 1100 psi.

SUMMARY

This disclosure is based, in part, on the realization that valve operations can be coordinated in such a manner as to reduce sample carry-over and system pressure perturbations occurring during introduction of a sample into a supercritical fluid chromatography (SFC) system.

One aspect provides a method that includes pressurizing a flow path connected to a separation column with a mobile phase fluid comprising liquefied $CO_2$; then pressurizing fluidic tubing and a sample loop containing a sample slug with the mobile phase fluid; and then establishing fluidic communication between the fluidic tubing and the separation column and thereby introducing the sample slug into the pressurized flow path (e.g., such that the sample slug is at substantially the same pressure as the flow path when it is introduced).

Another aspect provides an injection valve subsystem for introducing a sample slug into a mobile phase fluid flow in a supercritical fluid chromatography system. The subsystem includes an auxiliary valve and an inject valve. The auxiliary valve includes an auxiliary valve stator having a first plurality of stator ports, and an auxiliary valve rotor having a first plurality of grooves. The inject valve includes an inject valve stator having a second plurality of stator ports, and an inject valve rotor having a second plurality of grooves. A sample loop is fluidically connected to the inject valve stator for receiving a sample slug to be introduced into a mobile phase fluid flow, and fluidic tubing fluidically connects the auxiliary valve stator and the inject valve stator. The auxiliary valve rotor is rotatable, relative to the auxiliary valve stator, between a plurality of discrete positions to form different fluidic passageways within the auxiliary valve. The inject valve rotor is rotatable, relative to the inject valve stator, between a plurality of discrete positions to form different fluidic passageways within the inject valve. The respective positions of the auxiliary valve rotor and the inject valve rotor can be coordinated in such a manner as to allow the sample loop and the fluidic tubing to be pressurized to a high system pressure before they are placed in fluidic communication with a separation column fluidically connected to the auxiliary valve.

In another aspect, a supercritical fluid chromatography (SFC) system includes a separation column, one or more pumps for delivering a flow of a mobile phase fluid including $CO_2$ to the separation column, and an injection valve subsystem in fluidic communication with the one or more pumps and the separation column. The injection valve subsystem includes an auxiliary valve and an inject valve. The auxiliary valve includes an auxiliary valve stator having a first plurality of stator ports, and an auxiliary valve rotor having a first plurality of grooves. The inject valve includes an inject valve stator having a second plurality of stator ports, and an inject valve rotor having a second plurality of grooves. A sample loop is fluidically connected to the inject valve stator for receiving a sample slug to be introduced into a mobile phase fluid flow, and fluidic tubing fluidically connects the auxiliary valve stator and the inject valve stator. The auxiliary valve rotor is rotatable, relative to the auxiliary valve stator, between a plurality of discrete positions to form different fluidic passageways within the auxiliary valve. The inject valve rotor is rotatable, relative to the inject valve stator, between a plurality of discrete positions to form different fluidic passageways within the inject valve. The respective positions of the auxiliary valve rotor and the inject valve rotor can be coordinated in such a manner as to allow the sample loop and the fluidic tubing to be pressurized to a high system pressure before they are placed in fluidic communication with the separation column.

Yet another aspect provides a method that includes causing an auxiliary valve and an inject valve to operate cooperatively to pressurize a sample slug to system pressure before it is introduced into a pressurized flow path fluidically connected to a separation column; and then causing the auxiliary valve and the inject valve to operate cooperatively to introduce the pressurized sample slug into the pressurized flow path.

Implementations can provide one or more of the following advantages. The inherent characteristics of the SFC carrier solvent (liquid $CO_2$) can be detrimental to the integrity and the ability of an auto-sampler injection valve to inject a sample by conventional means (simple fixed loop or direct injection) due to the limitations on carrier solvent and the rapid decompression that occurs when liquid $CO_2$ is exposed to ambient conditions. Certain injection techniques can allow the decompression to occur without influencing the introduction of the sample into a pump—column flow stream.

Some implementations provide a valve sequencing technique that can help to reduce sample carry-over.

The addition of a second valve and tubing to the chromatography system causes a severe pressure drop at the head of the column when the valves are turned into a position where the sample is introduced to the column. Valve sequencing can help to reduce this pressure pulse. During an injection, system pressure pulses can negatively affect column life by creating reverse flow at the head of the column. In some cases, an auxiliary valve can be cycled to an intermediate fill position to prevent reverse flow from occurring at the head of the column by reducing the pressure pulse once the valve cycles to the inject position. Other aspects, features, and advantages are in the description, drawings, and claims.

BRIEF DESCRIPTION OF THE DRAWINGS

Like reference numbers indicate like elements.

DETAILED DESCRIPTION

System Overview

Figure 1:
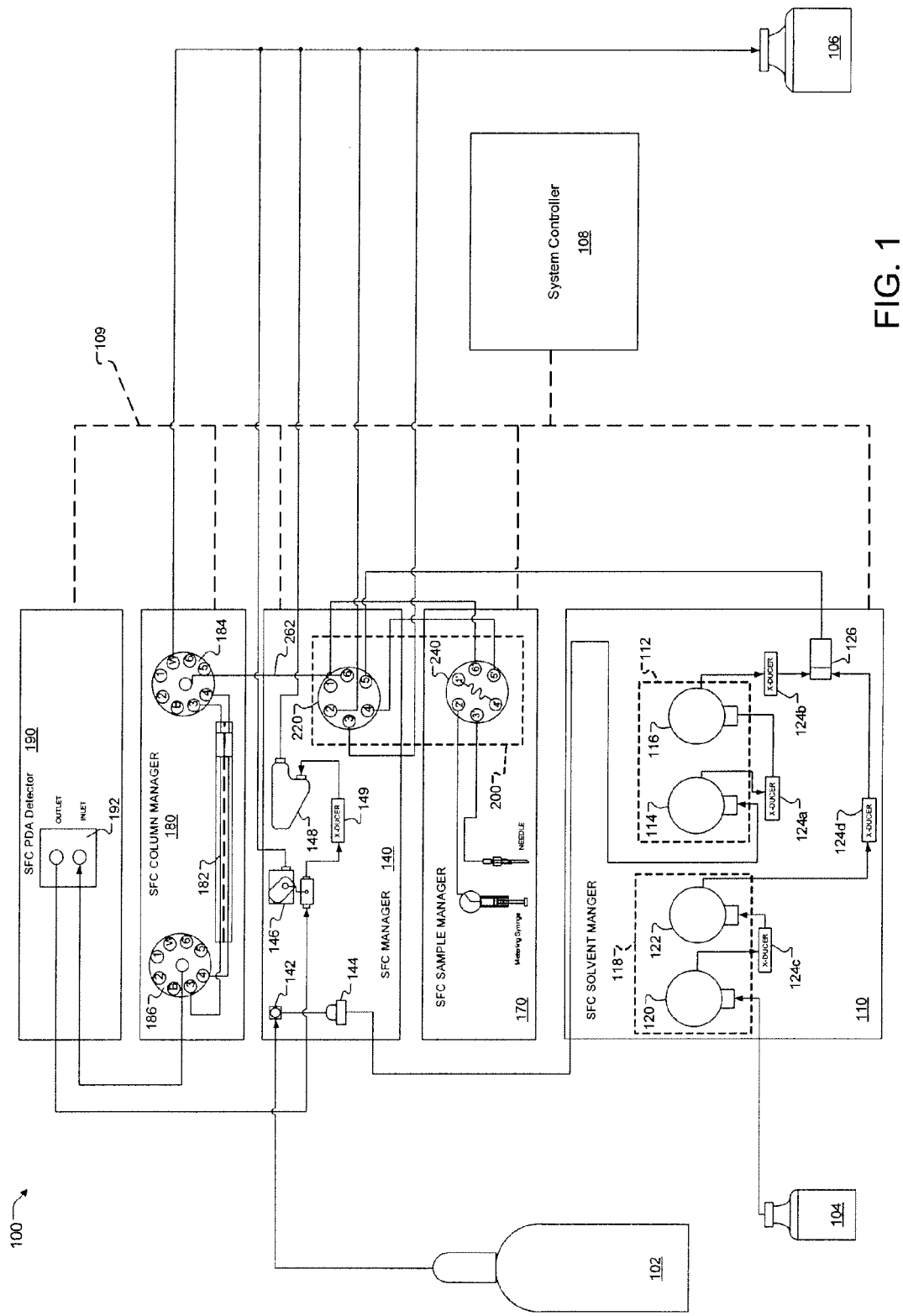
FIG. 1 is a schematic view of a supercritical fluid chromatography (SFC) system.

FIG. 1 schematically depicts a supercritical fluid chromatography (SFC) system 100. The SFC system 100 includes a plurality of stackable modules including a solvent manager 110; an SFC manager 140; a sample manager 170; a column manager 180; and a detector module 190.

The solvent manager 110 is comprised of a first pump 112 which receives carbon dioxide (CO2) from CO2 source 102 (e.g., a tank containing compressed CO2). The CO2 passes through an inlet shutoff valve 142 and a filter 144 in the SFC manager 140 on its way to the first pump 112. The first pump 112 can comprise one or more actuators each comprising or connected to cooling means, such as a cooling coil and/or a thermoelectric cooler, for cooling the flow of CO2 as it passes through the first pump 112 to help ensure that the CO2 fluid flow is deliverable in liquid form. In some cases, the first pump 112 comprises a primary actuator 114 and an accumulator actuator 116. The primary and accumulator actuators 114, 116 each include an associated pump head, and are connected in series. The accumulator actuator 116 delivers CO2 to the system 100. The primary actuator 114 delivers CO2 to the system 100 while refilling the accumulator actuator 116.

In some cases, the solvent manager 110 also includes a second pump 118 for receiving an organic co-solvent (e.g., methanol, water (H2O), etc.) from a co-solvent source 104 and delivering it to the system 110. The second pump 118 can comprise a primary actuator 120 and an accumulator actuator 122, each including an associated pump head. The primary and accumulator actuators 120, 122 of the second pump 118 are connected in series. The accumulator actuator 122 delivers co-solvent to the system 100. The primary actuator 120 delivers co-solvent to the system 100 while refilling the accumulator actuator 122.

Transducers 124a-d are connected to outlets of the respective pump heads for monitoring pressure. The solvent manager 110 also includes electrical drives for driving the primary actuators 114, 120 and the accumulator actuators 116, 122. The CO2 and co-solvent fluid flows are mixed at a tee 126 forming a mobile phase fluid flow that continues to an injection valve subsystem 200, which injects a sample slug for separation into the mobile phase fluid flow.

Notably, the injection valve subsystem 200 is comprised of an auxiliary valve 220 that is disposed in the SFC manager 140 and an inject valve 240 that is disposed in the sample manager 170. The auxiliary valve 220 and the inject valve 240 are fluidically connected and the operations of these two valves are coordinated in such a manner as to reduce sample carry-over and system pressure perturbations occurring during injection. The SFC manager 140 includes a valve actuator for actuating the auxiliary valve 220 and electrical drives for driving the valve actuations. Similarly, the sample manager 170 includes a valve actuator for actuating the inject valve and electrical drives for driving the valve actuations.

From the injection valve subsystem 200, the mobile phase flow containing the injected sample slug continues through a separation column 182 in the column manager 180, where the sample slug is separated into its individual component parts. The column manager 180 comprises a plurality of such separation columns, and inlet and outlet switching valves 184, 186 for switching between the various separation columns.

After passing through the separation column 182, the mobile phase fluid flow continues on to a detector 192 (e.g., a flow cell/photodiode array type detector) housed within the detector module 190 then through a vent valve 146 and then on to a back pressure regulator 148 in the SFC manager 140 before being exhausted to waste 106. A transducer 149 is provided between the vent valve 146 and the back pressure regulator 148.

The back pressure regulator 148 is adjustable to control or modify the system fluid pressure. This can allow the pressure to be changed from run to run. The properties of CO2 affect how quickly compounds are extracted from the separation column 182, so the ability to change the pressure can allow for different separation based on pressure. Generally, the back pressure regulator 148 can be used to maintain the system pressure in the range of about 1500 psi to about 6000 psi.

Also shown schematically in FIG. 1 is a computerized system controller 108 that can assist in coordinating operation of the SFC system 100. Each of the individual modules 110, 140, 170, 180, 190 also includes its own control electronics, which can interface with each other and with the system controller 108 via an Ethernet connection 109. The control electronics for each module can include non-volatile memory with computer-readable instructions (firmware) for controlling operation of the respective module's components (e.g., the pumps, valves, etc.) in response to signals received from the system controller 108 or from the other modules. Each module's control electronics can also include at least one processor for executing the computer-readable instructions, receiving input, and sending output. The control electronics can also include one or more digital-to-analog (DA) converters for converting digital output from one of the processors to an analog signal for actuating an associated one of the pumps or valves (e.g., via an associated pump or valve actuator). The control electronics can also include one or more analog-to-digital (AD) converters for converting an analog signal, such as from system sensors (e.g., pressure transducers), to a digital signal for input to one of the processors. In some cases, some or all of the various features of these control electronics can be integrated in a microcontroller.

Injection Valve Subsystem

Figure 2:
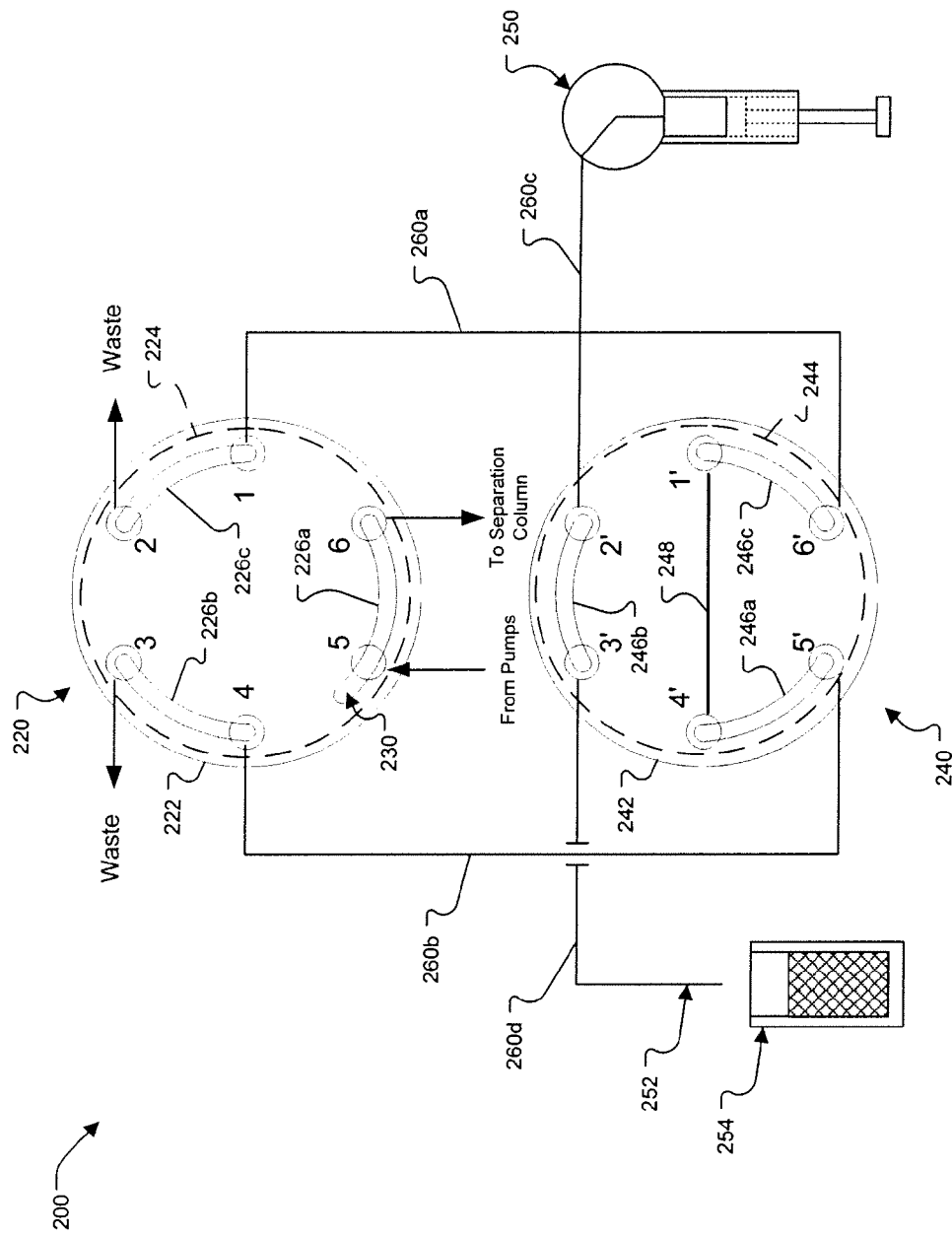
FIG. 2 is a schematic view of an injection valve subsystem of the SFC system of FIG. 1.

The injection valve subsystem 200 including the auxiliary valve 220 and the inject valve 240 is illustrated in FIG. 2. The auxiliary valve 220 is a rotary shear valve that includes an auxiliary valve stator 222 that has a plurality of ports, numbered 1 through 6 in FIG. 2, and an auxiliary valve rotor 224 that has a rotor interface, which includes three fluid conduits in the form of arcuate grooves 226a-c. When assembled, the rotor interface is urged into contact with the auxiliary valve stator 222, e.g., by pressure exerted on the auxiliary valve rotor 224 by a spring, to help ensure a fluid-tight seal therebetween. The ports 1-6 are configured to receive fittings (e.g., standard compression screw/ferrule type fittings) for coupling fluidic tubing to the auxiliary valve stator 222. The auxiliary valve rotor 224 can be rotated to three discrete angular positions, relative to the auxiliary valve stator 222, to connect the rotor grooves 226a-c with different ones of the stator ports 1-6 to form different fluidic passageways. Notably, one of the grooves, groove 226a, includes an extended portion 230 which allows the auxiliary valve rotor 224 to be rotated to a position in which the groove 226a forms a fluidic pathway between stator ports 4 and 5, while ports 1-3 and 6 are dead ended.

The inject valve 240 is another six-port rotary shear valve that includes an inject valve stator 242 having a plurality of ports, numbered 1' through 6' in FIG. 2, and an inject valve rotor 244. The inject valve rotor 244 has a rotor interface, which includes three fluid conduits in the form of arcuate grooves 246a-c. When assembled, the rotor interface is urged into contact with the inject valve stator 242, e.g., by pressure exerted on the inject valve rotor 244 by a spring, to help ensure a fluid-tight seal therebetween. The ports 1'-6' are configured to receive fittings (e.g., standard compression screw/ferrule type fittings) for coupling fluidic tubing to the inject valve stator 242. Port 1' is fluidically connected to port 4' via a sample loop 248 (e.g., fluidic tubing external to the inject valve stator 242). Port 2' is fluidically connected to a metering syringe 250 and port 3' is connected to a needle 252. The metering syringe 250 and needle 252 are disposed within the sample manager 170 and are operable to aspirate sample from vials 254 also in the sample manager 170. Port 5' of the inject valve 240 is connected to port 4 of the auxiliary valve 220, and port 6' of the inject valve 240 is connected to port 1 of the auxiliary valve 220. The connections between port 2' and the syringe 250, between port 3' and the needle 252, between port 5' and port 4, and between port 6' and port 1 are made via the fluidic tubing 260a-d.

The inject valve rotor 244 can be rotated to two discrete angular positions, relative to the inject valve stator 242, to connect the rotor grooves 246a-c with different ones of the stator ports 1'-6' to form different fluid passageways.

Method of Use

The coordinated operation of the auxiliary and inject valves 220, 240 can help to improve performance of the SFC system 100 by reducing the amount of sample carry-over and can also help to reduce system pressure perturbations occurring during injection. As a result, the separation column 182 may be subjected to lower pressure pulses, potentially increasing the life of the column 182.

In short, during an injection, sample inside the sample loop 248 is brought online to the fluidic tubing 260a, 260b connecting the auxiliary and inject valves 220, 240 while mobile phase fluid comprising high pressure $CO_2$ flows directly from the pumps 112, 118 to the separation column 182 via the auxiliary valve 220. The auxiliary valve 220 then allows the fluidic tubing 260a, 260b, comprising gaseous $CO_2$ and sample, to fill and compress with the mobile phase fluid before introducing the fluid into the high pressure (e.g., about 1500 psi to about 6000 psi) stream. The combination of these two actions can help to reduce (e.g., eliminate) carry-over anomalies and system pressure pulses when introducing sample into the high pressure stream. An exemplary process is described below.

Step 1: Sample Manager Setup

First, the sample manager 170 sets up internally by running various checks and setup procedures.

Step 2: De-Compress Sample Loop

Figure 3A:
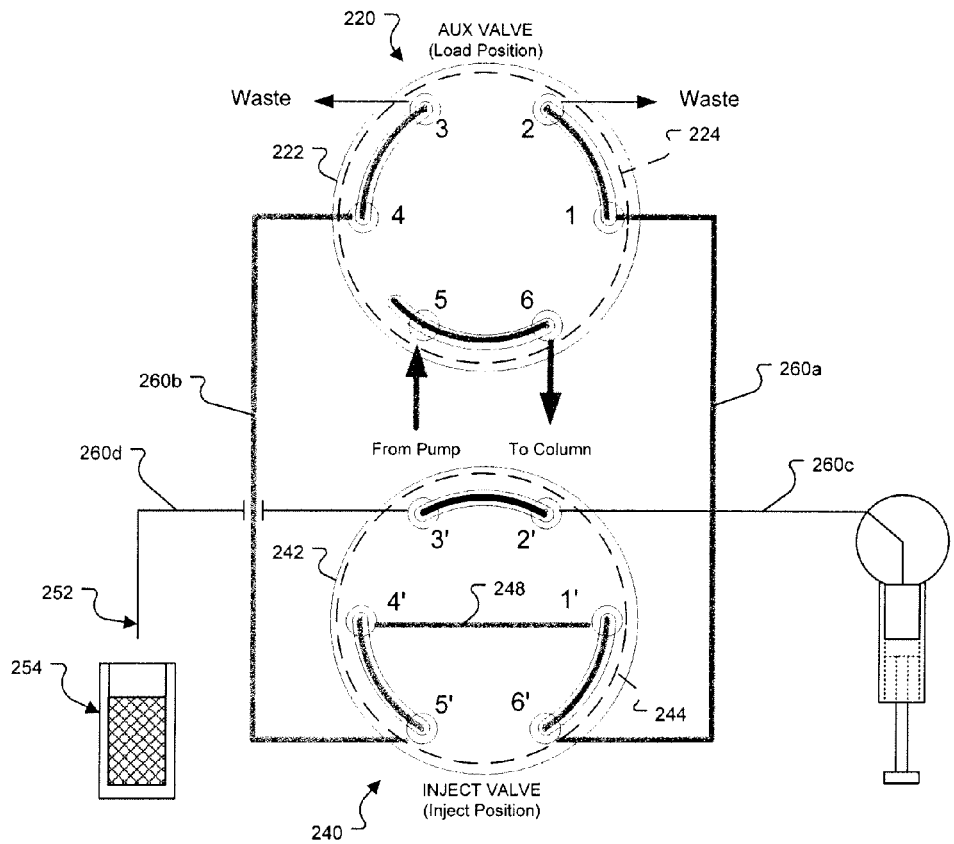
FIGS. 3A-3K illustrate an injection sequence of the injection valve subsystem of FIG. 2.
Figure 3A:
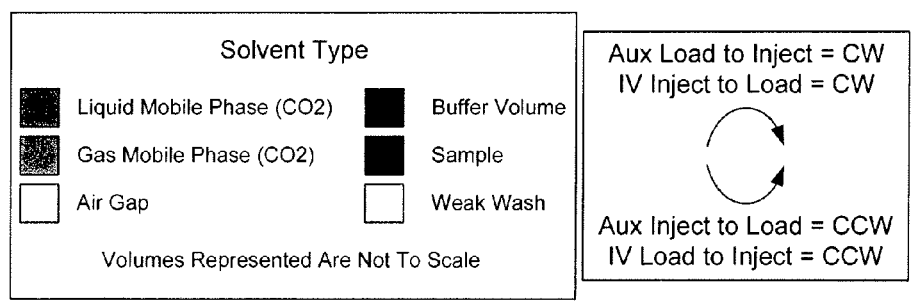

At the start of an injection, the inject valve rotor 244 is in its inject position (from a previous injection), and the sample manager 170 triggers the auxiliary valve 220 to turn its rotor 224 (60 degrees counterclockwise) to its load position. This allows the sample loop 248 on the inject valve 240 and the fluidic tubing 260a, 260b connecting the auxiliary and inject valves 220, 240 to vent to atmosphere. At this time, the mobile phase fluid is permitted to flow directly from the pumps 112, 118 to the separation column 182 via the auxiliary valve 220. This pressurizes a flow path 262 (FIG. 1) between the auxiliary valve 220 and the separation column 182 to a system pressure of about 1500 psi to about 3000 psi. FIG. 3A illustrates the respective positions of the auxiliary and inject valves 220, 240 during this decompression step. More specifically, FIG. 3A illustrates the auxiliary valve rotor 224 in its load position and the inject valve rotor 244 in its inject position with the sample loop 248 in fluid communication with the waste ports (i.e., ports 2 and 3) of the auxiliary valve 220.

Step 3: Aspirate Partial Loop with Needle Overfill (PLNO) Sample

Figure 3B:
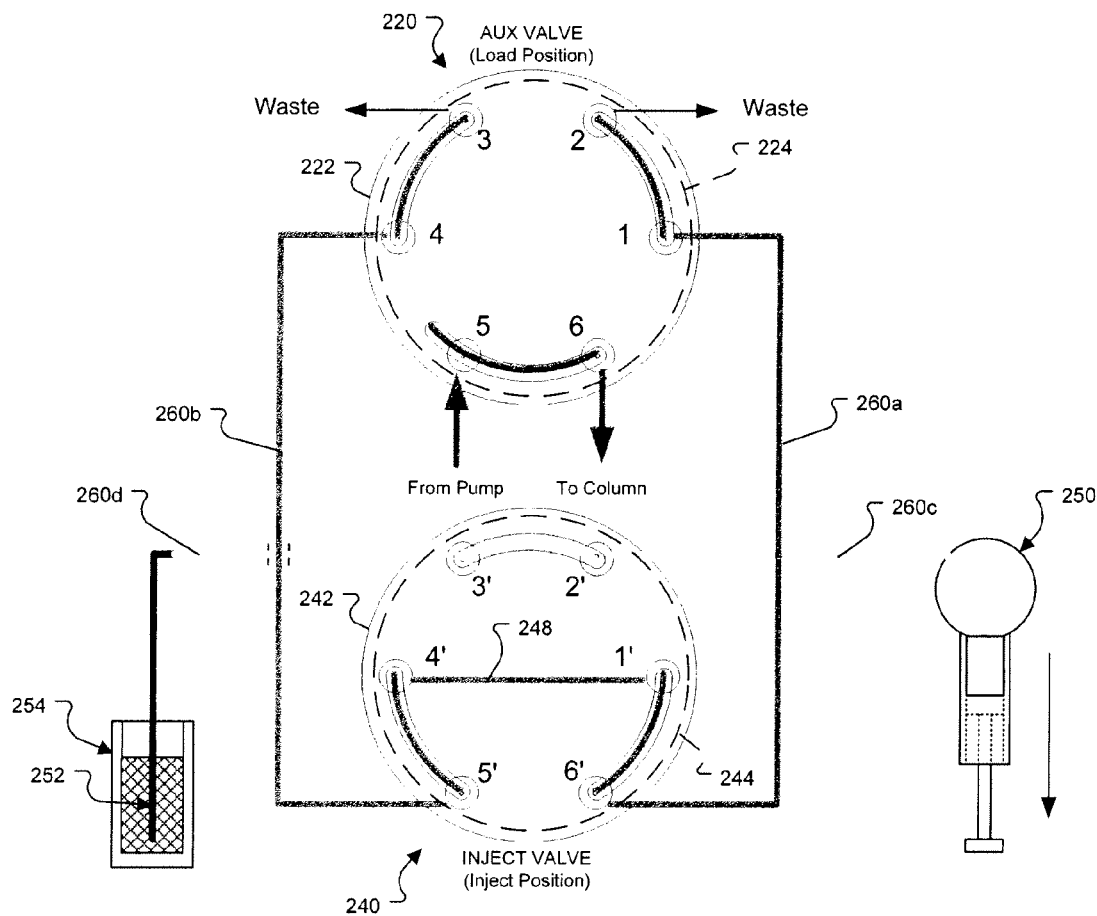
Figure 3C:
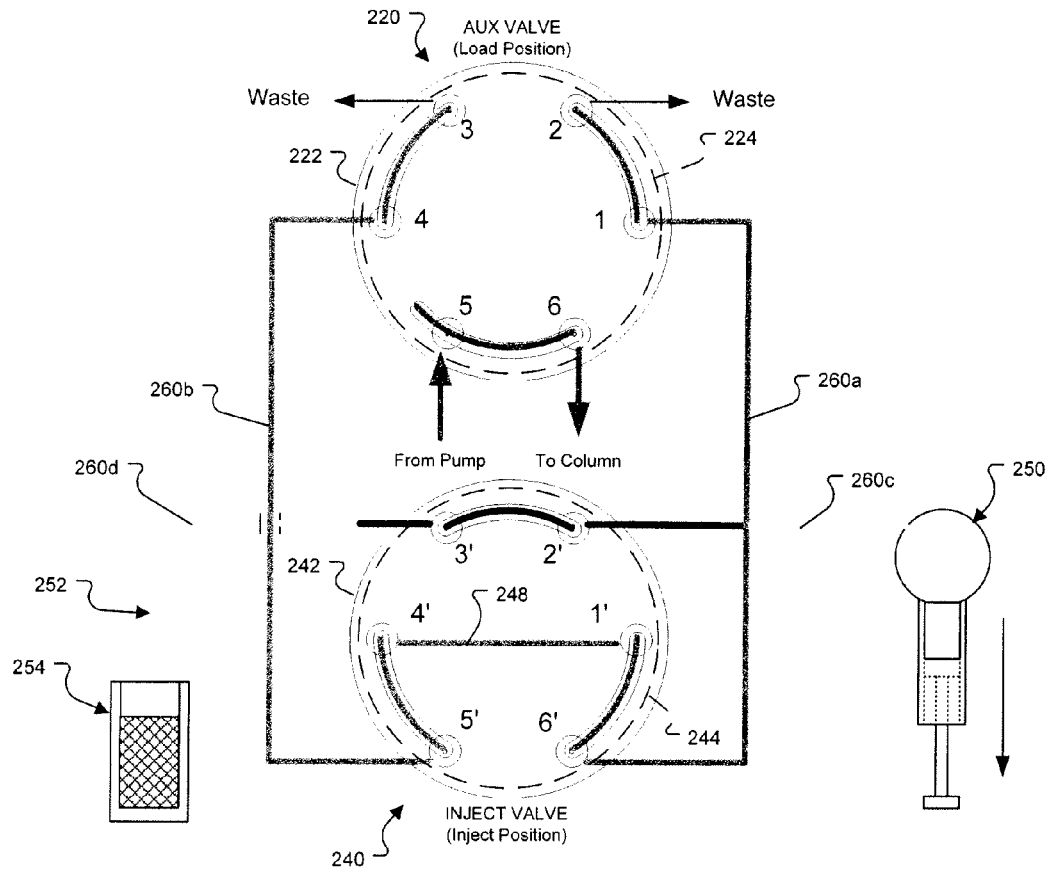
Figure 3D:
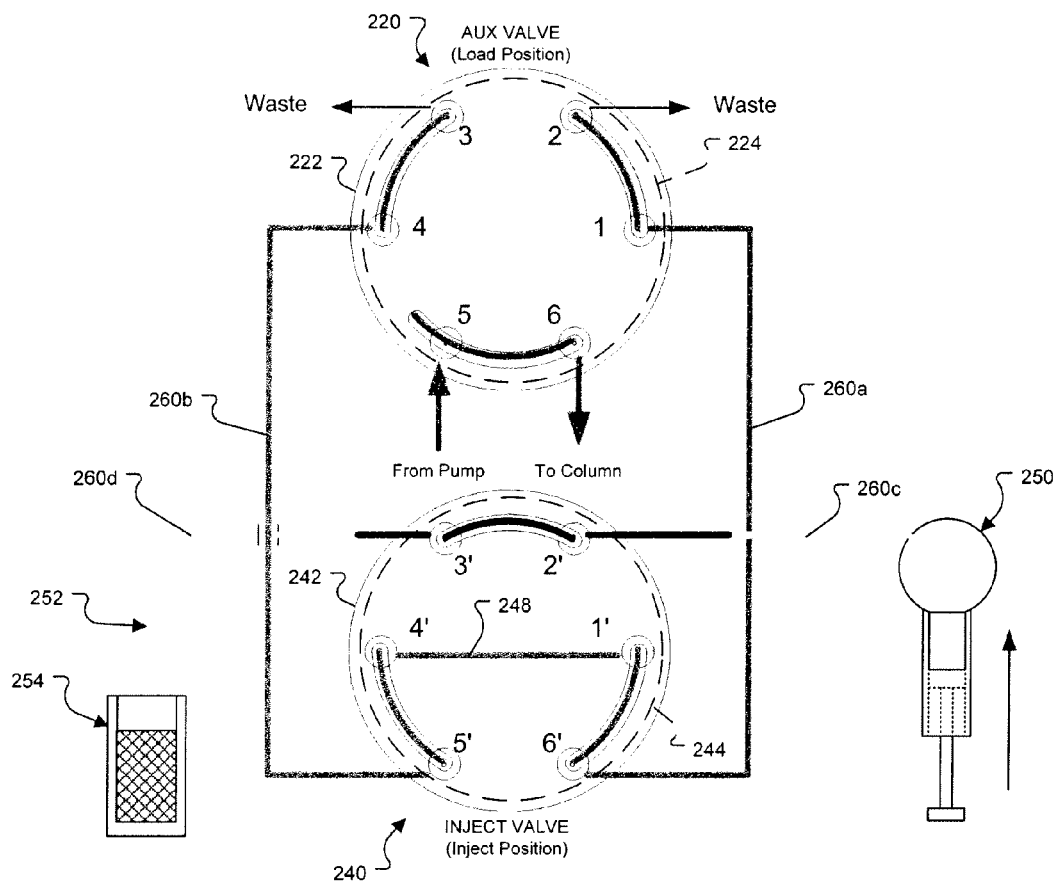

Next, the sample manager 170 moves the needle 252 to a programmed vial position, aspirates an air gap, aspirates pre-sample buffer from the vial 254, aspirates the programmed amount of sample from the vial 254, aspirates post-sample buffer from the vial 254 (see FIG. 3B), and then removes the needle 252 from the vial and returns it toward the inject port. A final air gap is aspirated in this position. Then, the sample manager metering syringe 250 meters the sample slug so that the injection volume is past port 2' (see FIG. 3C). The syringe 250 then dispenses 0.5 uL to take out any compliance or backlash within the system (see FIG. 3D).

Step 4: Load Sample into the Sample Loop

Figure 3E:
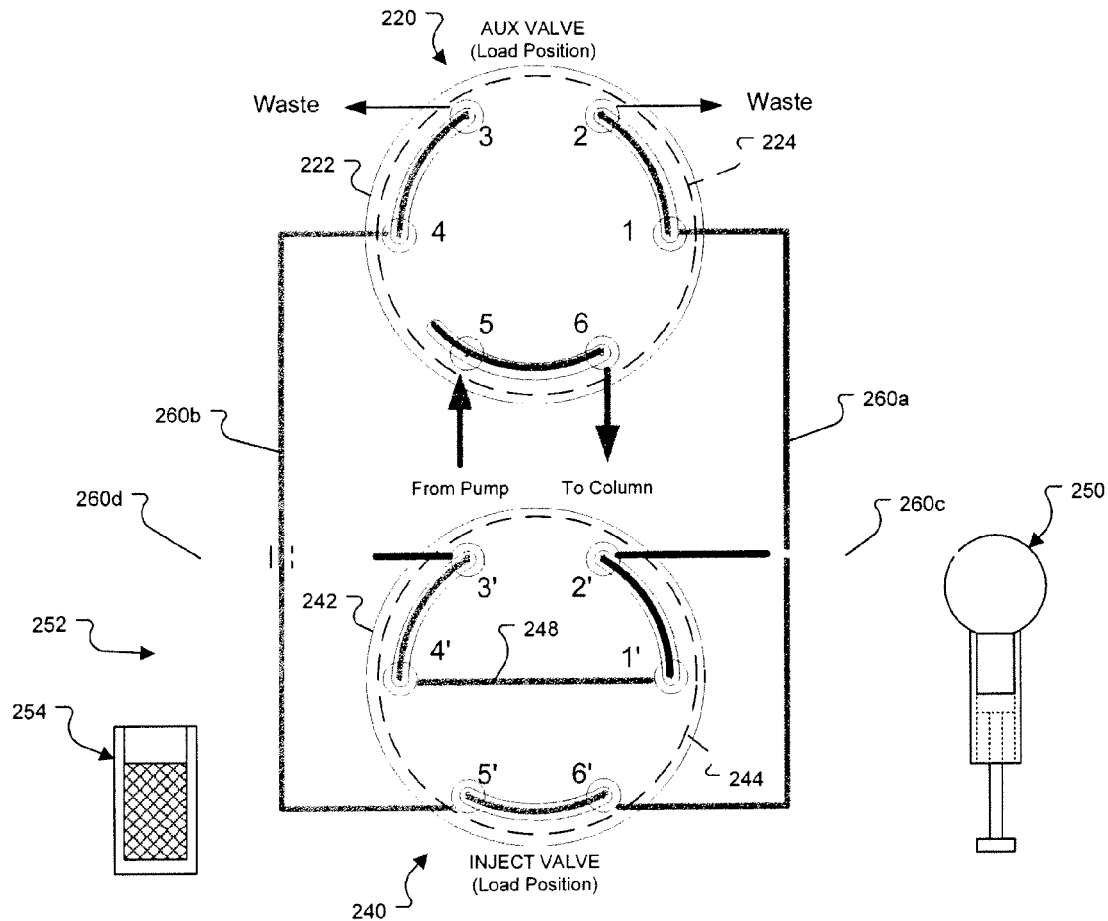
Figure 3E:
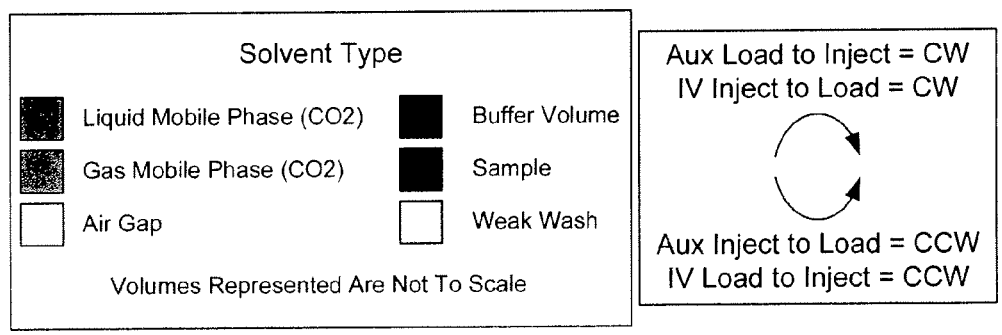
Figure 3F:
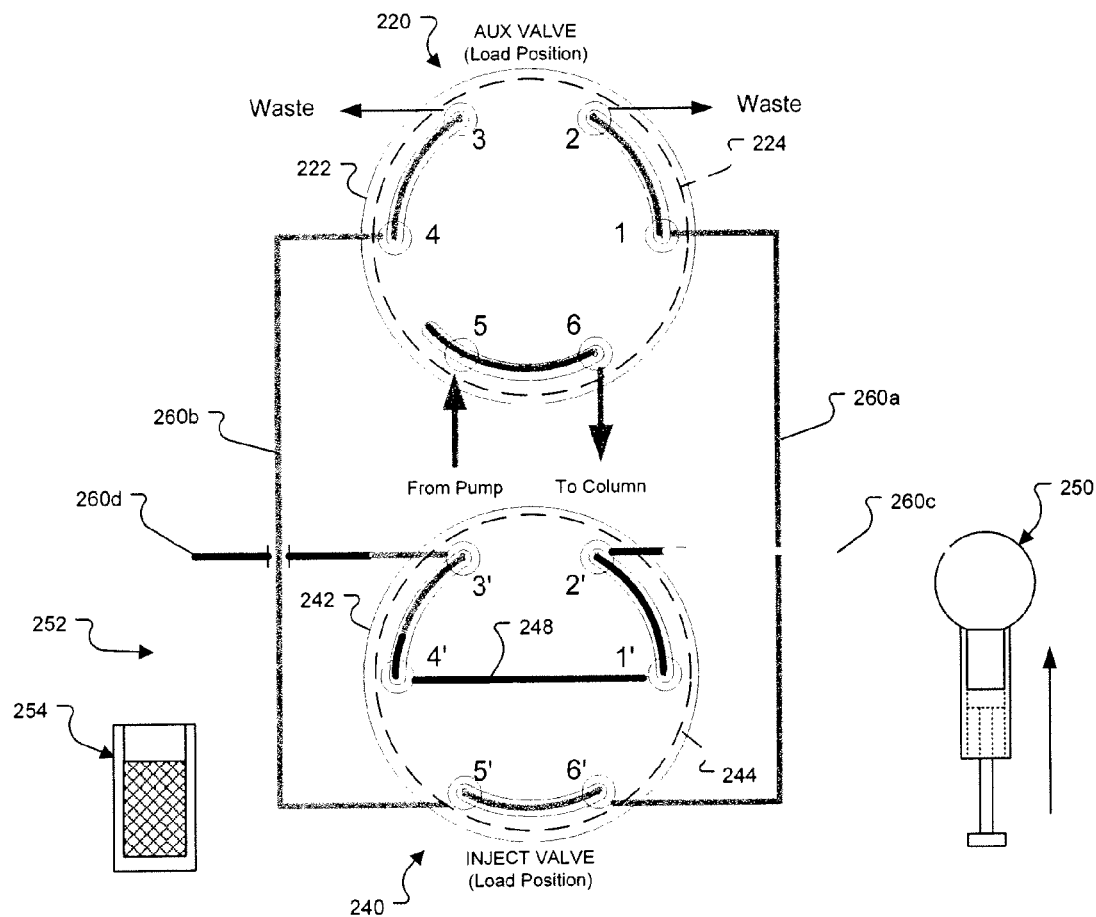

The inject valve rotor 244 is then moved (60 degrees clockwise) to place the inject valve 240 in its load position, with the sample loop 248 in fluidic communication with the meter and needle ports 2', 3' (see FIG. 3E), and the programmed sample volume is moved into the sample loop 248 (see FIG. 3F).

Step 5: Inject Sample into Fluidic Tubing

Figure 3G:
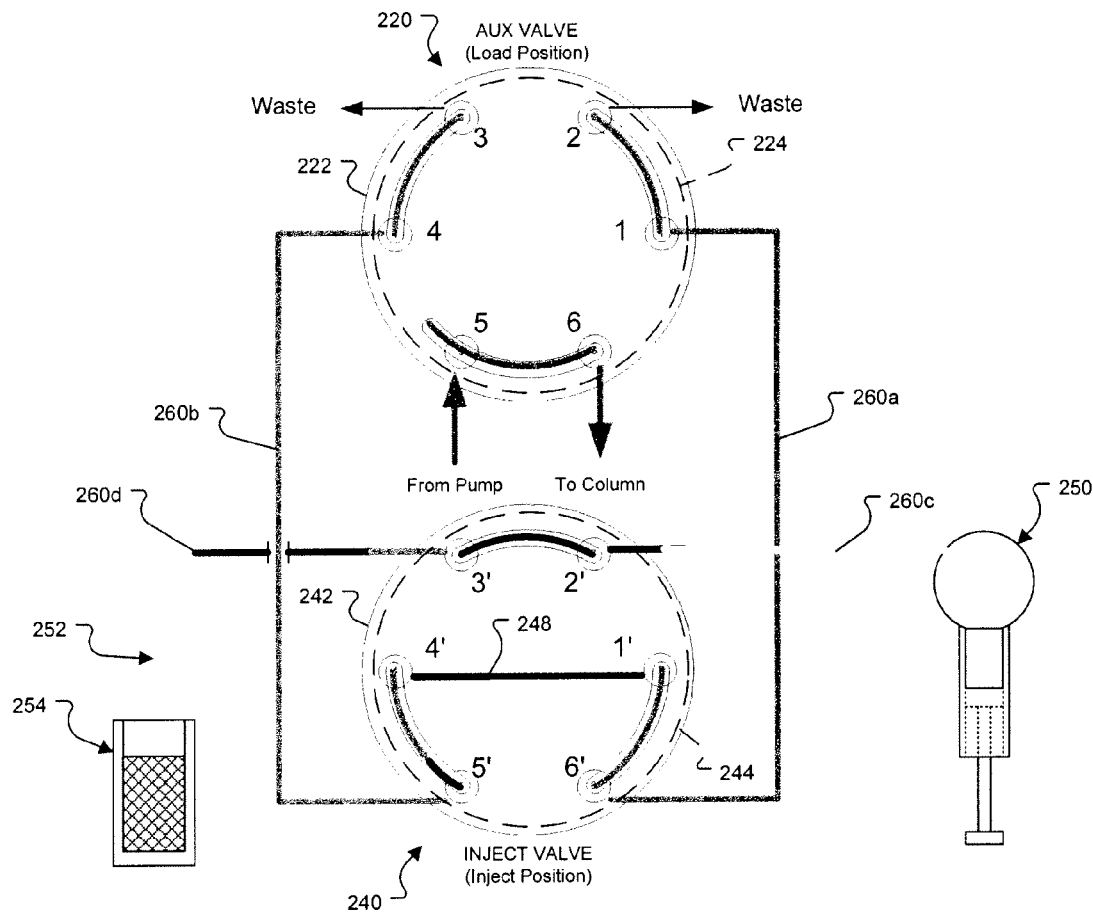

Within the sample manager 170, the inject valve rotor 244 is rotated (60 degrees counterclockwise) to the inject position, introducing sample into residual gaseous $CO_2$ and programmed co-solvent from the previous injection in the fluidic tubing 260a, 260b connecting the auxiliary and injection valves 220, 240 as illustrated in FIG. 3G.

Step 6: Bring $CO_2$ Online/Inject Sample into System

Figure 3H:
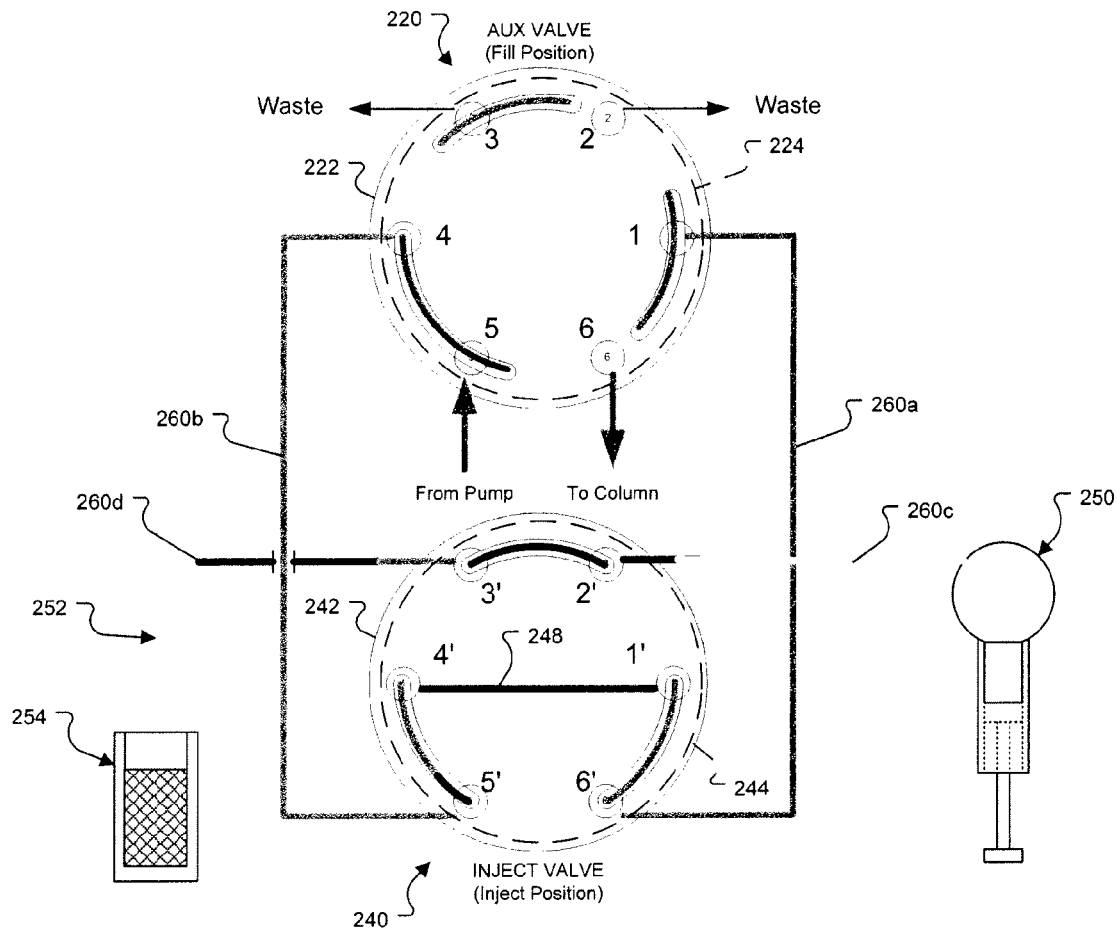
Figure 3H:
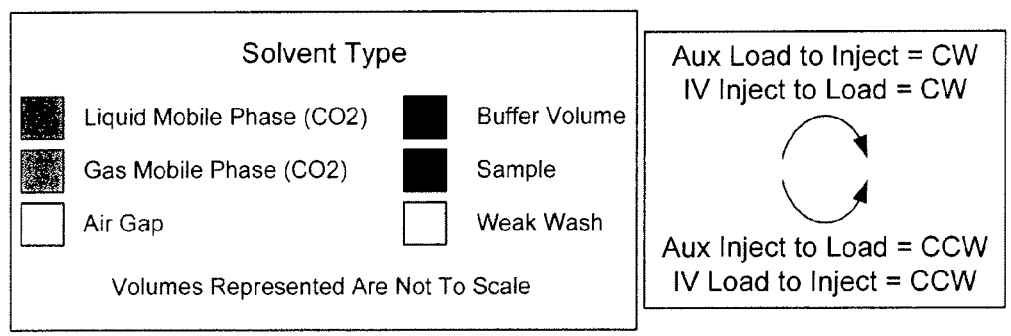
Figure 3I:
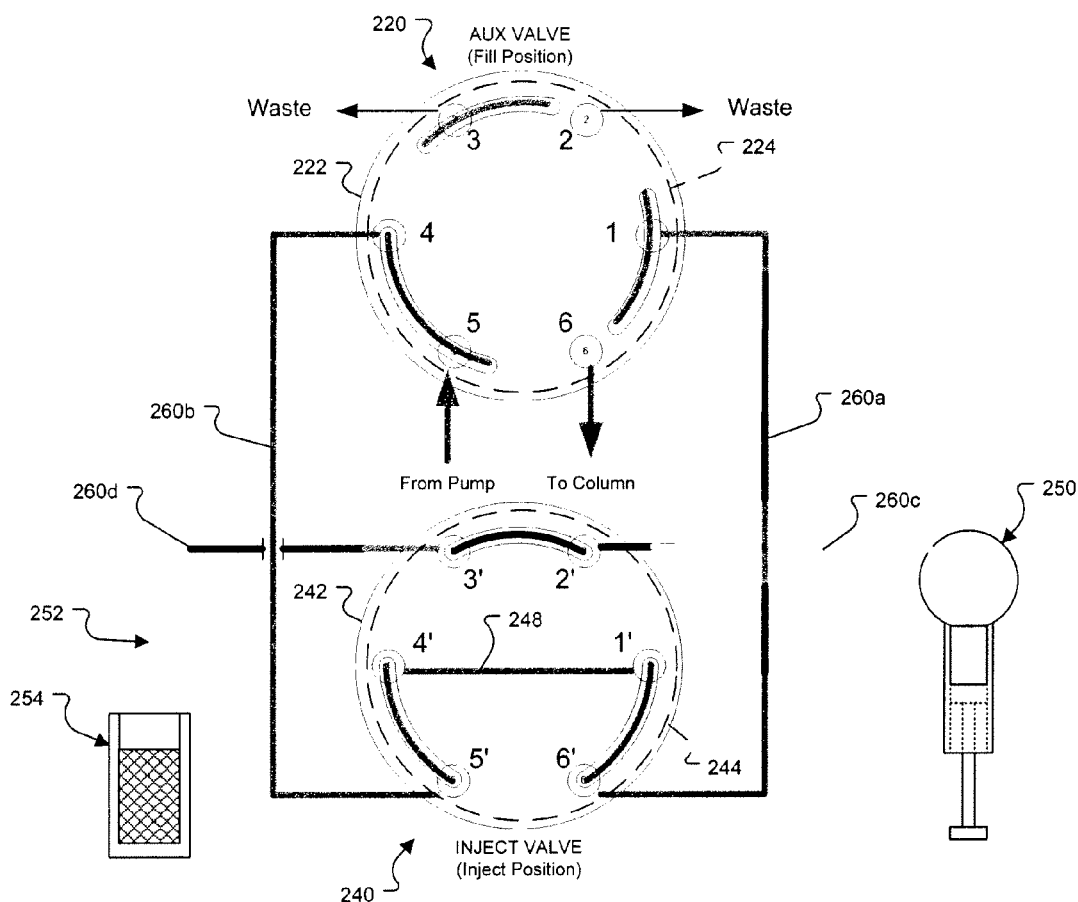

The sample manager 170 then triggers the auxiliary valve rotor 224 to turn (45 degrees clockwise) to place the auxiliary valve rotor 224 in its fill position to make the connection between ports 4 and 5 only. At this time, all other connections are dead ended. This action redirects the flow of mobile phase fluid comprising $CO_2$ and any programmed co-solvent from the pumps 112, 118 through the sample loop 248 and dead ends against port 1 of the auxiliary valve 220 (see FIG. 3H). The auxiliary valve rotor 224 remains in the fill position for a calculated pause time (based on mobile phase flow rate, sample loop 248 volume, and injection volume) until the fluidic tubing 260a, 260b and sample loop 248 are filled with liquid mobile phase comprising $CO_2$ and any programmed co-solvent(see FIG. 3I). During this time, the pressure in the flow path 262 between the auxiliary valve 220 and the separation column 182 remains substantially at system pressure (e.g., within 500 psi) due to the resistance to flow through the separation column 182. In this regard, the flow path 262 typically experiences a pressure drop of less than 500 psi while connections are dead ended.

Step 7: Inject Sample into System

Figure 3J:
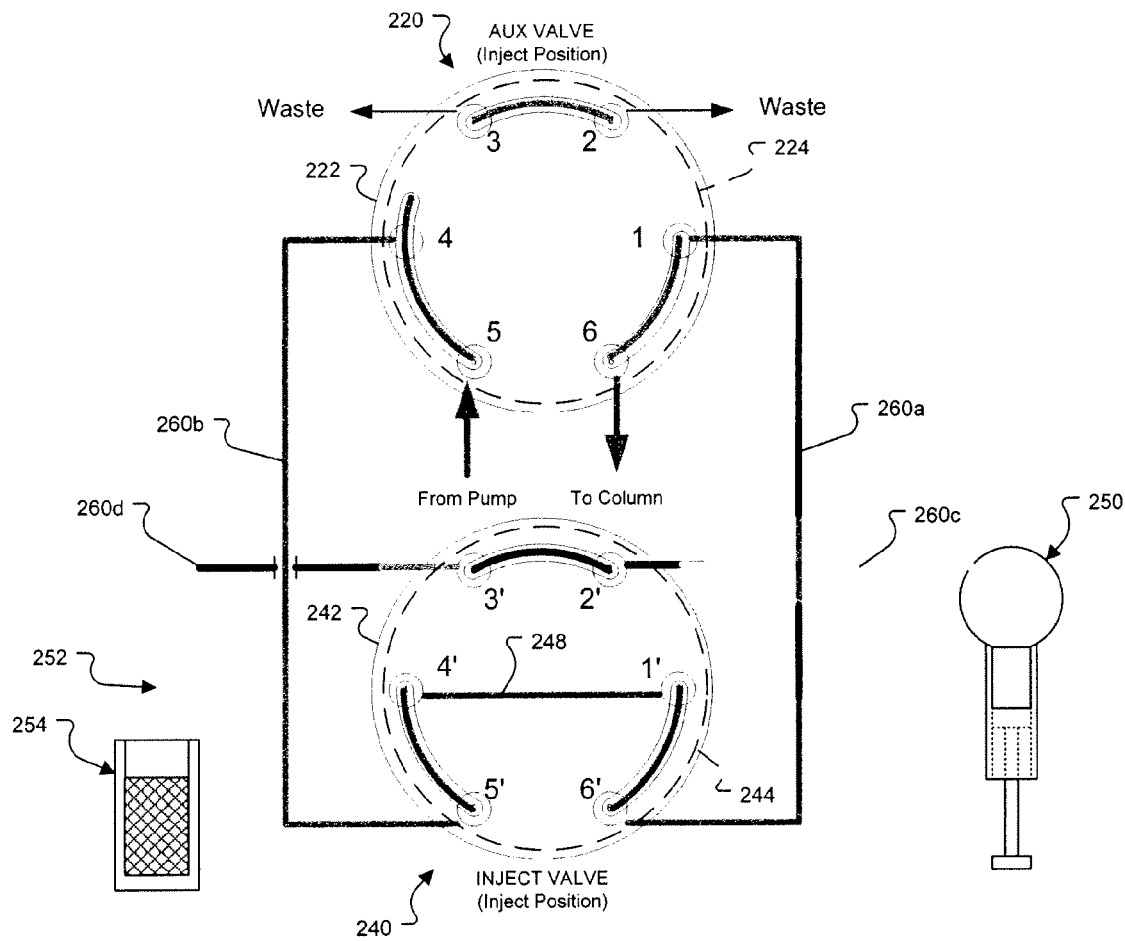
Figure 3J:
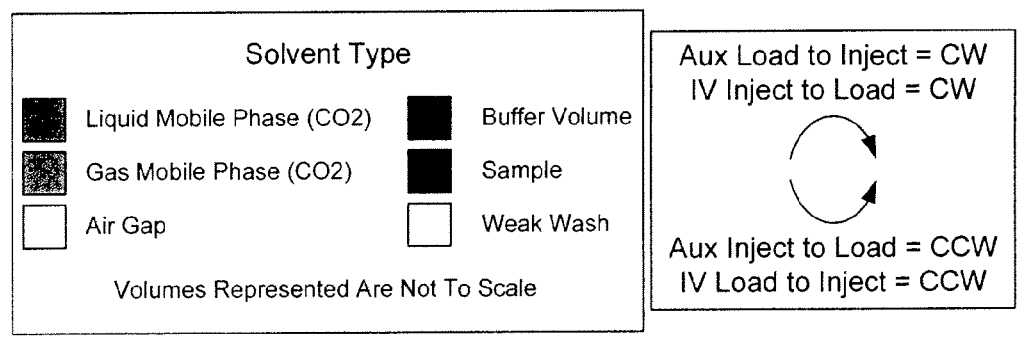

The auxiliary valve rotor 224 is then rotated (an additional 15 degrees clockwise) to the inject position, completing all port connections (see FIG. 3J). This action redirects the flow of mobile phase comprising high pressure $CO_2$ and any programmed co-solvent through the sample manager 170 and injects compressed sample into the high pressure system 100.

Step 8: Wash the Needle

Figure 3K:
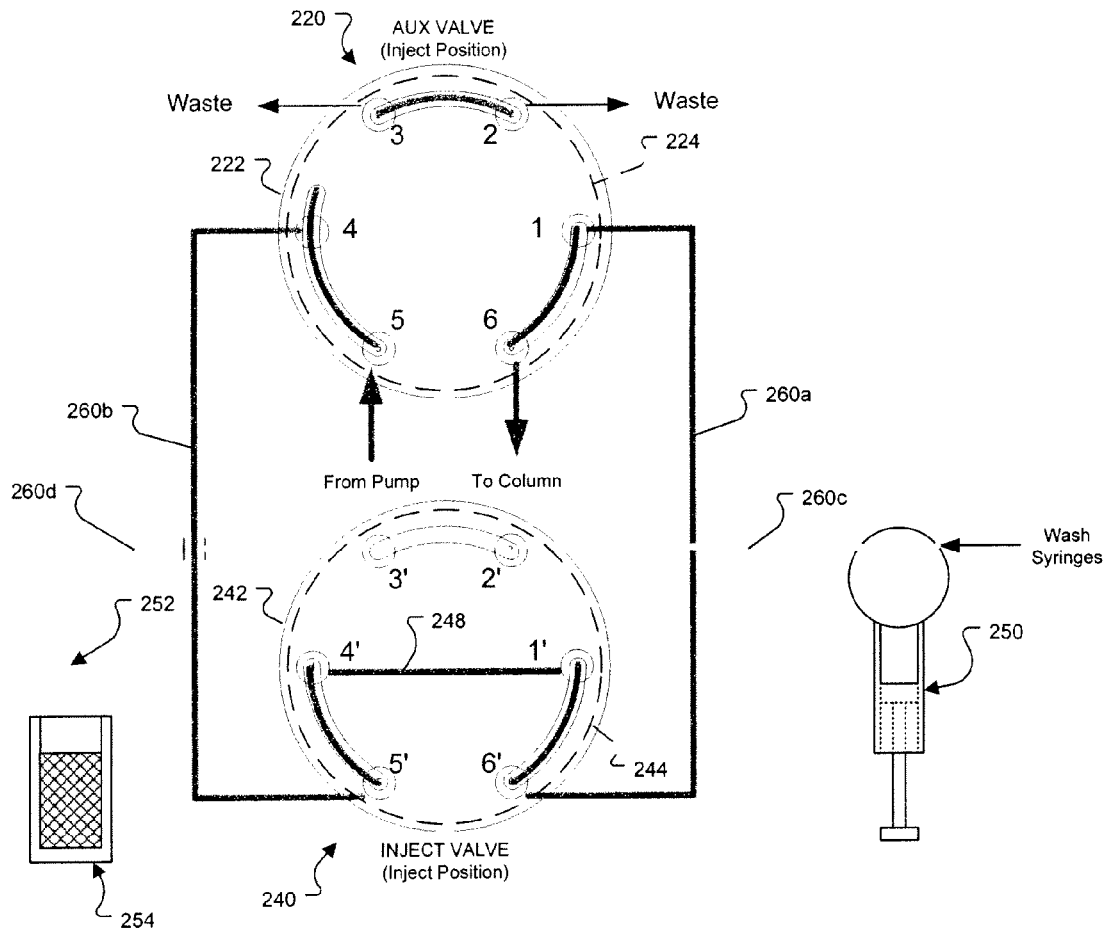

With the auxiliary and inject valve rotors 224, 244 in their respective inject positions, the sample manager 170 washes the outside and inside of the needle 252 after sample is injected. The wash syringes dispense a programmed amount of strong and weak washes through the inject valve 240 and out through the needle 252, as illustrated in FIG. 3K.

Figure 4:
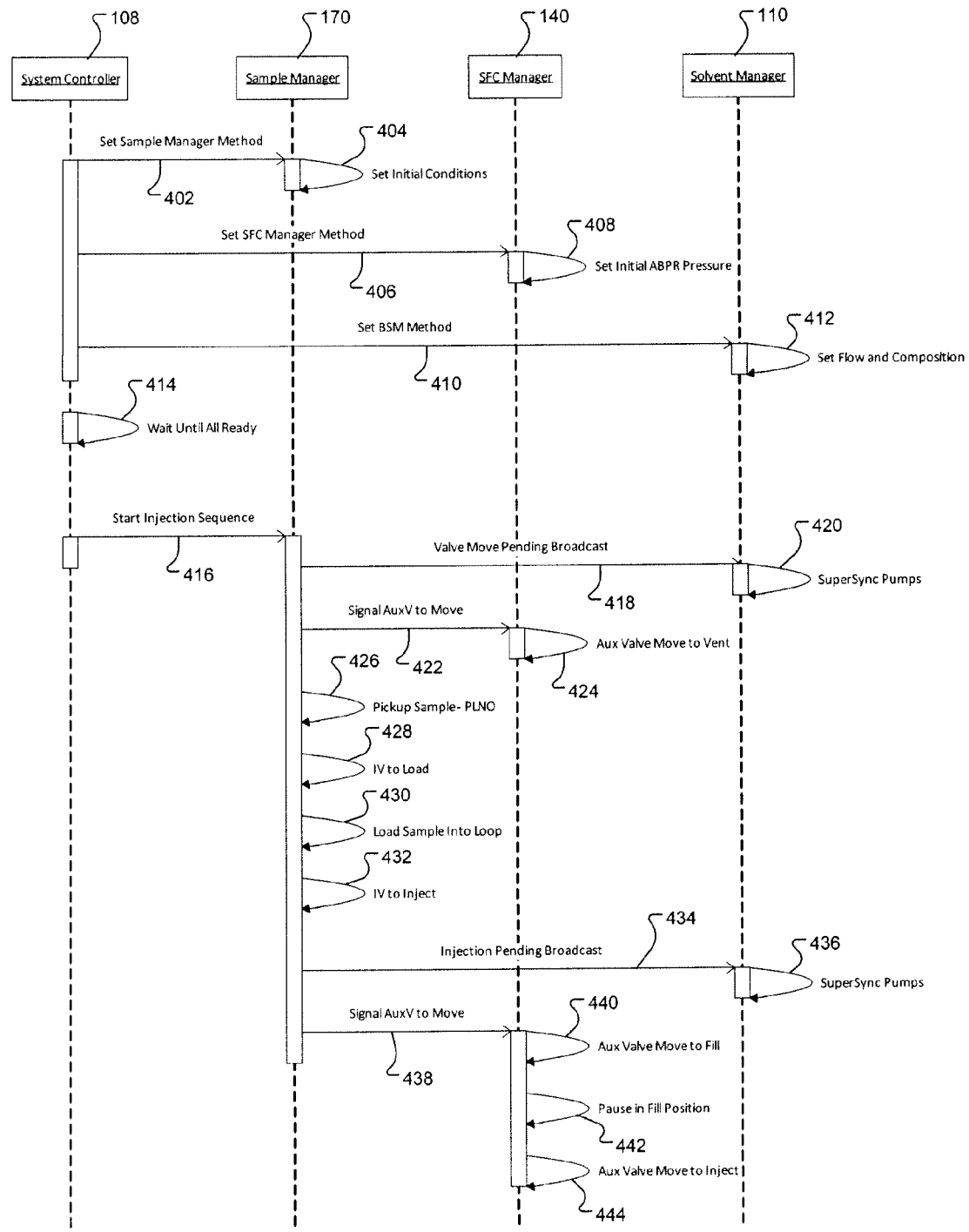
FIG. 4 is a software timing diagram used to develop the injection sequence.

FIG. 4 is a software timing diagram used to develop the injection sequence. With reference to FIG. 4, the system controller 108 signals (402) the sample manager 170, via the Ethernet connection, triggering the sample manager 170 to rotate (404) the inject valve rotor 244 to its inject position. The system controller 108 also signals (406) the SFC manager 140 to set (408) the back pressure regulator 148 to provide the desired pressure setting. Finally, the solvent manager 110 is triggered (410) by the controller 108 to set (412) the flow and composition of the mobile phase solvent. The system controller 108 waits (414) until the sample manager 170, SFC manager 140, and solvent manager 110 have performed their respective tasks and are ready to perform a sample injection.

Then, the system controller 108 signals (416) the sample manager 170 to start the injection sequence. In response, the sample manager 170 signals (418) the solvent manager 110 to synchronize (420) the pumps (positioning plungers within the actuators in a predetermined start point position). The sample manager 170 then signals (422) the SFC manager 140 to move (424) the auxiliary valve rotor 224 to its load position. Next, the sample manager 170 executes the step of aspirating the PLNO sample (426), and, then, drives (428) the inject valve rotor 244 to its load position. After sample is loaded (430) into the sample loop 248, the sample manager 170 drives (432) the inject valve to the inject position. The sample manager 170 then signals (434) the solvent manager 110 to again synchronize (436) the actuator plungers.

Finally, the sample manager 170 signals (438) the SFC manager 140 to execute the final movements of the auxiliary valve rotor 224. In response, the SFC manager 140 drives (440) the auxiliary valve rotor 224 to its fill position, and then pauses (442) it in the fill position (to fill and pressurize the fluidic tubing 260a, 260b with liquid mobile phase comprising CO2 and programmed co-solvent). Then, the SFC manager 140 drives (444) the auxiliary valve rotor 224 to its inject position (for injection of the sample into high pressure system).

Accordingly, other implementations are within the scope of the following claims.

What is claimed is:

1. A method comprising;
pressurizing a flow path connected to a separation column with a mobile phase fluid comprising liquefied $CO_2$; then
pressurizing fluidic tubing and a sample loop containing a sample with the mobile phase fluid; and then
establishing fluidic communication between the fluidic tubing and the separation column and thereby introducing the sample into the pressurized flow path;
wherein the flow path fluidically connects an auxiliary value and the separation column, and wherein the fluidic tubing fluidically connects the auxiliary valve and an inject value;
wherein the auxiliary valve comprises:
an auxiliary valve stator comprising a first plurality of stator ports; and
an auxiliary valve rotor comprising a first plurality of grooves wherein the auxiliary valve rotor is rotatable, relative to the auxiliary valve stator, between a plurality of discrete positions to form different fluidic passageways within the auxiliary valve;
wherein the inject valve comprises:
an inject valve stator comprising a second plurality of stator ports; and
an inject valve rotor comprising a second plurality of grooves, wherein the inject valve rotor is rotatable, relative to the inject valve stator, between a plurality of discrete positions to form different fluidic passageways within the inject valve;
wherein the respective position of the auxiliary valve rotor and the inject valve rotor are coordinated to form plurality of discrete configurations for performing the step of pressurizing the flow path, pressurizing the fluidic tubing and the sample loop, and establishing fluidic communication between the fluidic tubing and the separation column; and
wherein the step of establishing the fluidic communication between the fluidic tubing and the separation column is performed while the auxiliary valve rotor is in an inject position and the inject valve rotor is an inject position such that the mobile phase fluid flows from the one or more pumps to the auxiliary valve, then from the auxiliary valve to the inject vlave, and then back to the auxiliary valve, and then to the flow path.

2. The method claim 1, further comprising venting the fluidic tubing and the sample loop to atmospheric pressure.

3. The method of claim 1, further comprising venting the sample loop and the fluidic tubing to atmospheric pressure prior to pressurizing the fluidic tubing and the sample loop containing the sample.

4. The method of claim 1, wherein the step of pressurizing the fluidic tubing and the sample loop is performed while the inject valve rotor is in an inject position which places the sample loop in fluidic communication with the fluidic tubing.

5. The method of claim 1, wherein the step of pressurizing the fluidic tubing and the sample loop is performed while the auxiliary valve rotor is in a fill position which inhibits flow of the mobile phase fluid between the auxiliary valve and the column.

6. The method of claim 1, wherein pressurizing the flow path comprises delivering the mobile phase fluid from one or more pumps to the separation column through the auxiliary valve.

7. The method of claim 6, further comprising venting the sample loop and the fluidic tubing to atmospheric pressure prior to pressurizing the fluidic tubing and the sample loop containing the sample, wherein the venting step is performed while the mobile phase fluid is being delivered to the separation column.

8. The method of claim 1, wherein the step of pressurizing the flow path is performed while the auxiliary valve rotor is in a load position which allows the mobile phase fluid to flow from one or more pumps to the separation column through the auxiliary valve.

9. The method of claim 8, further comprising venting the sample loop and the fluidic tubing to atmospheric pressure while the auxiliary valve rotor is in the load position.

10. The method of claim 9, wherein the step of venting the sample loop is performed while the inject valve rotor is in an inject position which places the sample loop in fluidic communication with the fluidic tubing.

11. An injection valve subsystem for introducing a sample into a mobile phase fluid flow in a supercritical fluid chromatography system, the subsystem comprising:

I) an auxiliary valve comprising:
   A) an auxiliary valve stator comprising a first plurality of stator ports; and
   B) an auxiliary valve rotor comprising a first plurality of grooves,
II) an inject valve comprising:
   A) an inject valve stator comprising a second plurality of stator ports; and
   B) an inject valve rotor comprising a second plurality of grooves,
III) a sample loop fluidically connected to the inject valve stator for receiving the sample to be introduced into the mobile phase fluid flow; and
IV) fluidic tubing fluidically connecting the auxiliary valve stator and the inject valve stator,
wherein the auxiliary valve rotor is rotatable, relative to the auxiliary valve stator, between a plurality of discrete positions to form different fluidic passageways within the auxiliary valve;
wherein the inject valve rotor is rotatable, relative to the inject valve stator, between a plurality of discrete positions to form different fluidic passageways within the inject valve, and
wherein the respective positions of the auxiliary valve rotor and the inject valve rotor are coordinated in such a manner as to allow the sample loop and the fluidic tubing to be pressurized to a high system pressure before they are placed in fluidic communication with a separation column fluidically connected to the auxiliary valve;
wherein the respective positions of the auxiliary valve rotor and the inject valve rotor are coordinated to provide;
   a first configuration that allows the fluidic tubing and the sample loop to vent to atmospheric pressure via the auxiliary valve;
   a second configuration that allows the sample loop to be loaded with the sample while the fluidic tubing vents to atmosphere;
   a third configuration that allows first and second fluidic tubing and the sample loop to be pressurized via a flow of a mobile phase fluid one or more pumps connected to the auxiliary valve; and
   a fourth configuration that allows the sample to be delivered from the sample loop to a separation column fluidically connected to the auxiliary valve.

12. A supercritical fluid chromatography (SFC) system comprising:
   I) a separation column;
   II) one or more pumps for delivering a flow of a mobile phase fluid comprising $CO_2$ to the separation column; and
   III) an injection valve subsystem according to claim 11, in fluidic communication with the one or more pumps and the separation column, wherein the auxiliary valve stator is in fluidic communication with the one or more pumps and the separation column.

13. The injection valve subsystem of claim 11, wherein the first plurality of ports comprises:
   a first port fluidically connected to the first fluidic tubing;
   a second port for venting to atmospheric pressure;
   a third port for venting to atmospheric pressure;
   a fourth port fluidically connected to the fluidic tubing;
   a fifth port for fluidically connecting the auxiliary valve to a pump; and
   a sixth port for fluidically connecting the auxiliary valve to a separation column; and wherein the second plurality of ports comprises:
   a seventh port fluidically connected to the sample loop;
   an eighth port for fluidically connecting the inject valve to a metering syringe;
   a ninth port for fluidically connecting the inject valve to a needle for aspirating the sample;
   a tenth port fluidically connected to the seventh port via the sample loop;
   an eleventh port fluidically connected to the fourth port via the fluidic tubing; and
   a twelfth port fluidically connected to the first port via the fluidic tubing.

14. The injection valve subsystem of claim 13, wherein the fluidic tubing comprises:
   a first fluidic tube fluidically connecting the first port and the twelfth port; and
   a second fluidic tube fluidically connecting the fourth port and the eleventh port.

15. The injection valve subsystem of claim 13, wherein the first plurality of grooves comprises:
   a first groove;
   a second groove; and
   a third groove, and
   wherein the auxiliary valve rotor is rotatable between three discrete positions relative to the auxiliary valve stator including:
      a load position in which the first groove fluidically connects the fifth and sixth ports, the second groove fluidically connects the third and fourth ports, and the third groove fluidically connects the first and second ports;
      a fill position in which the first groove fluidically connects the fourth and fifth ports, and in which the first, second, third and sixth ports are dead ended; and
      an inject position in which the first groove fluidically connects the fourth and fifth ports, the second groove fluidically connects the second and third ports, and the third groove fluidically connects the first and sixth ports.

16. The injection valve subsystem of claim 15, wherein the second plurality of grooves comprises:
   a fourth groove;
   a fifth groove; and
   a sixth groove,
   wherein the inject valve rotor is rotatable between two discrete positions relative to the inject valve stator including:
      an inject position in which the fourth groove fluidically connects the tenth and eleventh ports, the fifth groove fluidically connects the eighth and ninth ports, and the sixth groove fluidically connects the seventh and twelfth ports; and
      a load position in which the fourth groove fluidically connects the ninth and tenth ports, the fifth groove fluidically connects the seventh and eighth ports, and the sixth groove fluidically connects the eleventh and twelfth ports.

17. The injection valve subsystem of claim 16, wherein in the first configuration the auxiliary valve rotor is in its load position and the inject valve rotor is in its inject position.

18. The injection valve subsystem of claim 16, wherein in the second configuration the auxiliary valve rotor is in its load position and the inject valve rotor is in its load position.

19. The injection valve subsystem of claim 16, wherein in the third configuration the auxiliary valve rotor is in its fill position and the inject valve rotor is in its inject position.

20. The injection valve subsystem of claim 16, wherein in the fourth configuration the auxiliary valve rotor is in its inject position and the inject valve rotor is in its inject position.

* * * * *